(12) United States Patent
Nie (10) Patent No.: US 10,940,263 B2
(45) Date of Patent: Mar. 9, 2021

(54) SINGLE STEP REMOVAL OF CANNULA GUARD AND ADHESIVE LINER IN MEDICAL DEVICE

(71) Applicant: Becton, Dickinson and Company, Franklin Lakes, NJ (US)

(72) Inventor: Weiyan Nie, Winchester, MA (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 288 days.

(21) Appl. No.: 13/784,721

(22) Filed: Mar. 4, 2013

(65) Prior Publication Data
US 2014/0249502 A1 Sep. 4, 2014

(51) Int. Cl.
| A61M 5/00 | (2006.01) |
| A61M 5/162 | (2006.01) |
| A61M 5/158 | (2006.01) |
| A61B 17/34 | (2006.01) |
| A61M 5/32 | (2006.01) |
| A61B 5/00 | (2006.01) |
| A61B 5/145 | (2006.01) |

(52) U.S. Cl.
CPC ....... *A61M 5/1626* (2013.01); *A61B 17/3421* (2013.01); *A61M 5/158* (2013.01); *A61M 5/3202* (2013.01); *A61B 5/14532* (2013.01); *A61B 5/6865* (2013.01); *A61M 2005/1586* (2013.01)

(58) Field of Classification Search
CPC .......... A61M 2005/1585; A61M 5/002; A61M 5/158; A61M 5/1626
USPC .... 60/174, 180, 162, 164.08, 192, 198, 263; 604/174, 180, 162, 164.08, 192, 198, 263
See application file for complete search history.

(56) References Cited

U.S. PATENT DOCUMENTS

| 2,392,351 | A | * | 1/1946 | Wolf ................................ 40/1.5 |
| 4,755,173 | A | | 7/1988 | Konopka et al. |
| 4,858,358 | A | * | 8/1989 | Gagnon .......................... 40/616 |
| 5,050,323 | A | * | 9/1991 | Gagnon ........................... 40/1.5 |
| 5,191,682 | A | * | 3/1993 | Davis-Reardon et al. ....... 24/13 |
| 5,451,725 | A | * | 9/1995 | Goldman ...................... 181/131 |
| 5,716,343 | A | * | 2/1998 | Kriesel ............... A61M 5/1409 128/DIG. 12 |
| 5,851,197 | A | * | 12/1998 | Marano et al. ................ 604/135 |

(Continued)

FOREIGN PATENT DOCUMENTS

| JP | 2007-295998 A | 11/2007 |
| JP | 2009-515673 A | 4/2009 |

(Continued)

OTHER PUBLICATIONS

"Cleo 90 Infusion Set Training Guide", Smiths Medical ASD, Inc., Feb. 2011.

(Continued)

*Primary Examiner* — William R Carpenter
(74) *Attorney, Agent, or Firm* — Dickinson Wright PLLC (57) ABSTRACT

A medical device includes a body and a cannula extending from the body, for insertion into a patient's skin. The medical device also includes a guard covering the cannula, an adhesive for securing the medical device to the patient's skin, and an adhesive liner covering the adhesive. The guard is connected to the adhesive liner to enable conjoint and at least partial removal of the guard and the adhesive liner.

13 Claims, 7 Drawing Sheets

(56) References Cited

U.S. PATENT DOCUMENTS

| | | |
|---|---|---|
| 6,485,473 B1 | 11/2002 | Lynn |
| 6,685,674 B2 | 2/2004 | Douglas et al. |
| 6,997,907 B2 * | 2/2006 | Safabash ............... A61M 5/158 604/157 |
| 7,070,580 B2 | 7/2006 | Nielsen |
| 7,309,326 B2 | 12/2007 | Fangrow, Jr. |
| 7,331,939 B2 * | 2/2008 | Fangrow, Jr. ............ 604/167.02 |
| 7,520,867 B2 * | 4/2009 | Bowman ............... A61M 25/02 604/174 |
| 7,584,527 B2 * | 9/2009 | Jones ............................... 24/3.3 |
| 7,621,395 B2 * | 11/2009 | Mogensen et al. ........... 206/365 |
| 7,850,658 B2 | 12/2010 | Faust et al. |
| 7,892,216 B2 | 2/2011 | Fangrow, Jr. |
| 7,935,096 B2 * | 5/2011 | Johansson et al. ........... 604/338 |
| 8,317,759 B2 * | 11/2012 | Moberg et al. ............... 604/263 |
| 8,414,563 B2 * | 4/2013 | Kamen et al. ............. 604/890.1 |
| 2005/0065466 A1 | 3/2005 | Vedrine |
| 2007/0021729 A1 * | 1/2007 | Mogensen ............ A61M 5/002 604/500 |
| 2007/0135774 A1 | 6/2007 | Turner et al. |
| 2009/0069750 A1 * | 3/2009 | Schraga ............ A61M 5/14248 604/167.02 |
| 2009/0143763 A1 | 6/2009 | Wyss et al. |
| 2010/0274200 A1 | 10/2010 | Nielsen |
| 2011/0112484 A1 * | 5/2011 | Carter ................. A61M 5/1626 604/180 |
| 2011/0152778 A1 * | 6/2011 | Gyrn ..................... A61F 13/023 604/180 |
| 2012/0004621 A1 * | 1/2012 | Shaw et al. .................... 604/221 |
| 2012/0022459 A1 * | 1/2012 | Horvath ................ A61M 5/002 604/192 |
| 2012/0071835 A1 * | 3/2012 | Marshall ............. A61M 5/3213 604/192 |
| 2012/0220956 A1 | 8/2012 | Kuracina et al. |
| 2013/0165866 A1 | 6/2013 | Christensen |

FOREIGN PATENT DOCUMENTS

| | | | |
|---|---|---|---|
| JP | 2013-514132 A | 4/2013 | |
| WO | WO-2007000162 A2 | 1/2007 | |
| WO | WO-2011075101 | 6/2011 | |
| WO | WO-2012030316 | 3/2012 | |
| WO | 2013086463 A1 | 6/2013 | |
| WO | WO 2013086463 A1 * | 6/2013 | ............ A61M 5/158 |

OTHER PUBLICATIONS

"Changing the Quikset Infusion Set Using a Revel Insulin Pump" Instructions Manual, Medtronic MiniMed, Inc., Oct. 2011.

* cited by examiner

SINGLE STEP REMOVAL OF CANNULA GUARD AND ADHESIVE LINER IN MEDICAL DEVICE

FIELD OF THE INVENTION

The present invention relates to medical devices, and more particularly, to medical devices with a cannula and an adhesive for securing the device to a patient's skin.

BACKGROUND OF THE INVENTION

Medical devices that are intended to deliver medicament or monitor patient conditions over an extended period of time are often designed to be worn by the patient. Many of these devices have a medical pressure sensitive adhesive to secure the device to the patient's skin as well as a cannula that is inserted through the patient's skin for delivering the medicament.

Insulin infusion sets designed for connection to insulin pumps are examples of these types of medical devices. Infusion pumps offer the advantages of continuous infusion of insulin, precision dosing, and programmable delivery schedules. Together, these advantages result in more accurate blood glucose control. With infusion sets, the types and sizes of the cannula may vary, but generally, the cannula is a thin, flexible tube. In some uses, however, it may be larger and/or rigid, for example, a rigid, hollow, metal needle. For insertion of a flexible cannula, a rigid introducer needle may be used.

One type of conventional infusion set is sold as the Quick-Set® infusion set by Medtronic. In such devices, the infusion set is connected to a pump via a tubing set, and a separate insertion device inserts and/or attaches the cannula assembly into/to a user via an introducer needle provided as part of the infusion set. The infusion set and insertion device can also be combined, as in the Mio® infusion set sold by Medtronic, which is an "all-in-one" design that combines the infusion set and insertion device into one unit.

Another type of insulin infusion device, known as a "patch pump," has recently become available. Unlike a conventional infusion pump, a patch pump is an integrated device that combines most or all of the fluid components in a single housing that is adhesively attached to an infusion site, and does not require the use of a separate infusion (tubing) set. A patch pump adheres to the skin, contains insulin (or other medication), and delivers the drug over a period of time via an integrated subcutaneous mini-catheter. Some patch pumps communicate with a separate controller device wirelessly (such as one sold under the brand name OmniPod®), while others are completely self-contained.

On-body continuous glucose monitoring (CGM) devices are also examples of medical devices with an insertable cannula and an adhesive to secure the device to the patient's skin.

To protect the cannula and/or introducer needle in the packaging and prior to insertion (as well as protect against accidental needle-stick injuries), conventional devices often include a cannula guard (sometimes referred to as a needle guard) that is removed prior to use. These needle guards, however, are often very small and may be difficult to grasp, particularly for people with impaired dexterity. To remove such needle guards, patients pull and/or twist the needle guard, and the axial force required to remove such needle guards may vary widely, for example, based on manufacturing tolerances.

The medical pressure sensitive adhesive (sticky layer) is typically covered by a release liner that has a silicone covering on one side to that permits the liner to release from the adhesive. Many adhesive release liners are divided into two or more pieces by slits, each of which should be removed prior to insertion of the device into a patient's skin. For people with impaired dexterity, these pieces may be difficult to grasp and remove.

Currently, patients have to remove the needle guard and peel off adhesive release liner in separate steps before they either directly apply the device onto their body or assemble the medical device into an insertion device. For example, with a conventional insulin infusion set, a user first peels off the adhesive liner(s), then assembles the infusion set into the inserter. Subsequently, the user pushes the needle guard inside the inserter to engage the set with the inserter and to load the inserter (for example, to load the spring). Finally, the user twists or pulls off the needle guard. During this process, exposed adhesive can catch on the user's finger or the inner wall of the inserter, potentially requiring the use of a new infusion set.

SUMMARY OF EMBODIMENTS OF THE INVENTION

Accordingly, it is an aspect of the present invention to provide a medical device in which the adhesive liner and the cannula guard can be removed in a single step.

The foregoing and/or other aspects of the present invention are achieved by providing a medical device, including a body and a cannula extending from the body, for insertion into a patient's skin. The medical device also includes a guard covering the cannula, an adhesive for securing the medical device to the patient's skin, and an adhesive liner covering the adhesive. The guard is connected to the adhesive liner to enable conjoint and at least partial removal of the guard and the adhesive liner.

The foregoing and/or other aspects of the present invention are also achieved by providing a method of preparing a medical device for insertion into a patient's skin. The method includes conjointly and at least partially removing a cannula guard and an adhesive liner from the medical device.

The foregoing and/or other aspects of the present invention are also achieved by providing a method of preparing a medical device for insertion into a patient's skin. The method includes providing a guard for covering an insertable cannula of the medical device, and providing an adhesive liner for protecting an adhesive surface and/or adhesive pad of the medical device. The method also includes connecting the needle guard to the adhesive liner so that removal of one of the guard and the adhesive liner from the medical device also at least partially removes the remaining one of the guard and the adhesive liner.

The foregoing and/or other aspects of the present invention are also achieved by providing a protector for a medical device, including a guard for covering a cannula of the medical device, and an adhesive liner for covering an adhesive for securing the medical device to a patient's skin. The guard is connected to the adhesive liner to enable conjoint and at least partial removal of the guard and the adhesive liner.

The foregoing and/or other aspects of the present invention are also achieved by providing a method of preparing a medical device for insertion into a patient's skin. The method includes installing the medical device into an insertion device, and subsequent to such installation, conjointly and at least partially removing a cannula guard and an adhesive liner from the medical device.

Additional and/or other aspects and advantages of the present invention will be set forth in the description that follows, or will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, in which.

DETAILED DESCRIPTION OF EMBODIMENTS OF THE PRESENT INVENTION

Reference will now be made in detail to embodiments of the present invention, which are illustrated in the accompanying drawings, wherein like reference numerals refer to like elements throughout. The embodiments described herein exemplify, but do not limit, the present invention by referring to the drawings. As will be understood by one skilled in the art, terms such as up, down, bottom, and top are relative, and are employed to aid illustration, but are not limiting.

Figure 1:
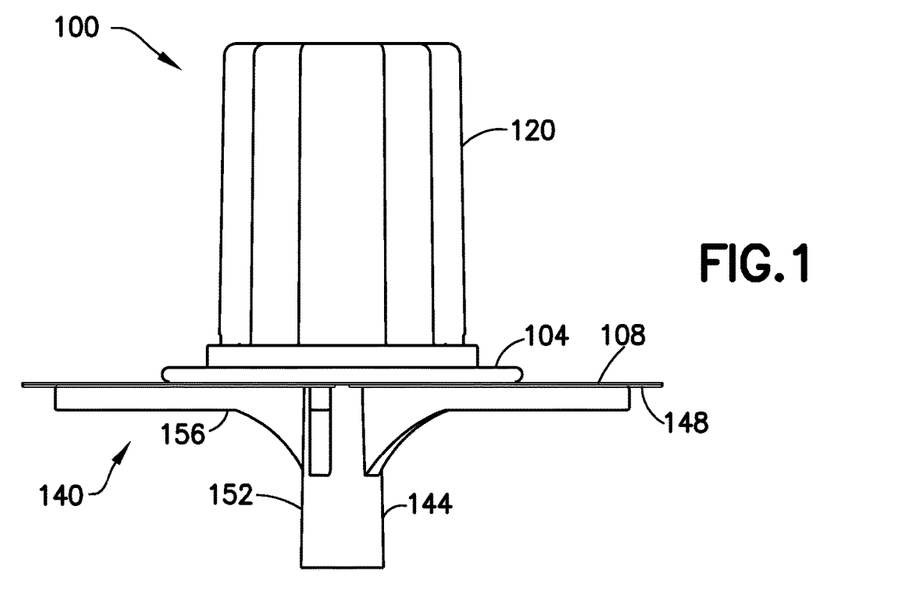
FIG. 1 is a perspective front view of a medical device in accordance with an embodiment of the present invention.
Figure 2:
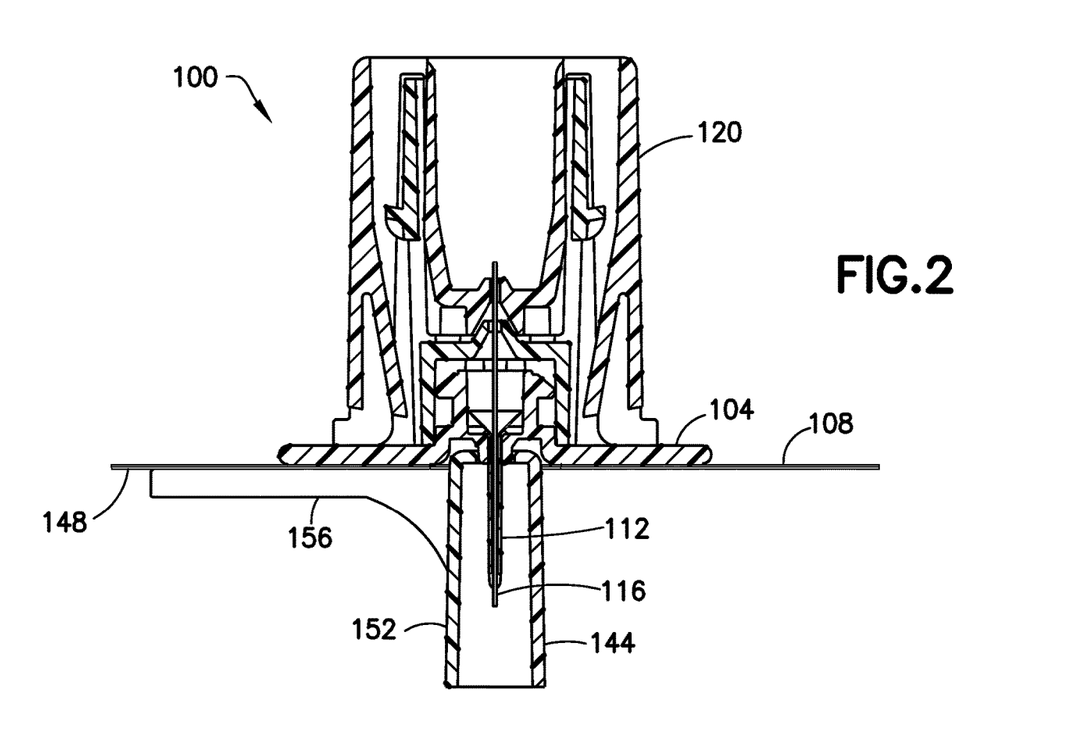
FIG. 2 is a cross-sectional view of the device of FIG. 1.

FIG. 1 is a perspective front view of a medical device 100 in accordance with an embodiment of the present invention, and FIG. 2 is a cross-sectional view of the device 100. The device 100 includes a base 104 with an adhesive pad 108 secured to its distal side for securing the device 100 to a patient's skin. An insertable cannula 112 depends from the distal side of the base 104. According to one embodiment, the cannula 112 is a flexible cannula 112 and the device 100 includes an introducer needle 116 with a user interface or handle 120 for removing the introducer needle 116 from the base 104. One skilled in the art will appreciate, however, that other cannulas can be used without departing from the scope of the present invention. The medical device 100 also includes a protector 140.

Figure 3:
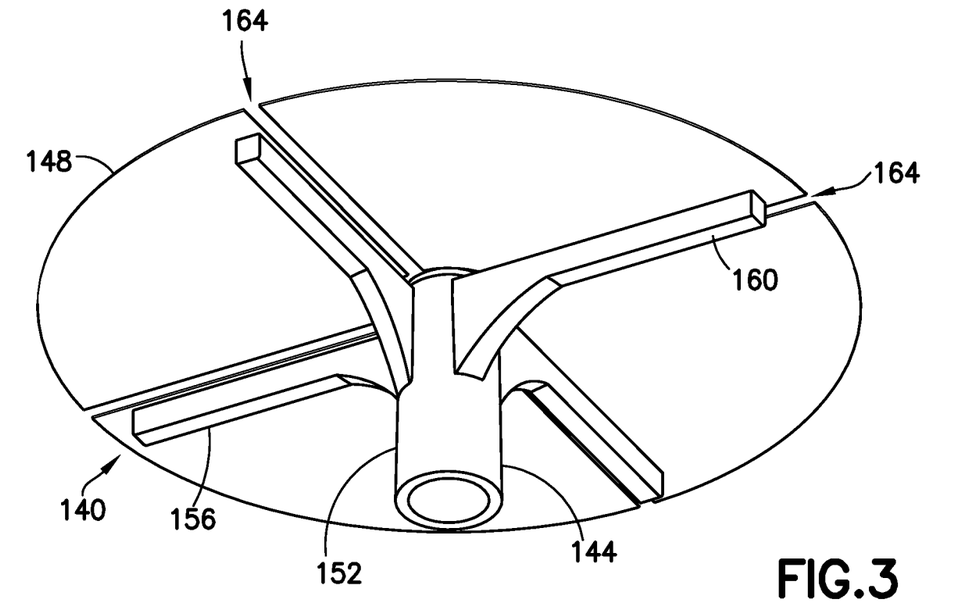
FIG. 3 is a bottom perspective view of a protector in accordance with an embodiment of the present invention.

As shown in FIGS. 1-3, according to one embodiment, the protector 140 includes a guard 144 covering the cannula 112 and the introducer needle 116, and an adhesive liner 148 covering the adhesive pad 108 and connected to the guard 144. The nature of the connection between the adhesive liner 148 and the guard 144 is such that removing one will also at least partially remove the other. In other words, the adhesive liner 148 and the guard 144 are operatively interrelated. Put another way, the adhesive liner 148 and the guard 144 are coupled. For example, according to one embodiment, the adhesive liner 148 and the guard 144 are joined directly to each other, for example, by an adhesive, such as a liquid instant adhesive. According to another embodiment, another element or elements can intercede between, but mechanically join the adhesive liner 148 and the guard 144. For example, double-sided tape can be used to join the adhesive liner 148 and the guard 144. As another example, a strip of paper, plastic, metal, string, or other material can be connected at one end to the adhesive liner 148 and be connected at another end to the guard 144. According to one embodiment, the strip is flexible. According to an alternative embodiment, the strip is rigid.

The guard 144 includes a guarding portion 152 for covering the cannula 112 and the introducer needle 116, and a connecting portion 156 for connecting with the adhesive liner 148. As shown in FIG. 3, the guarding portion 152 is open at its distal end. According to another embodiment (shown in FIG. 8, for example), the guarding portion is enclosed at its distal end.

According to one embodiment, the connecting portion 156 includes an arm 160 extending from the guarding portion 152. As shown in FIG. 3, the connecting portion 156 includes a plurality of arms 160, specifically, four arms 160. It will be understood, that the number of arms can be greater or lesser without departing from the scope of the present invention. The arms 160 are substantially straight, and are cantilevered from the guarding portion 152.

In addition, as shown in FIG. 3, the liner 148 has a plurality of slits 164 corresponding to the plurality of arms 160. One skilled in the art will appreciate that that the liner 148 can have a number of slits that is different from the number of arms without departing from the scope of the present invention. Preferably, the arms 160 are connected to the liner 148 at or adjacent to the respective slits 164, although the liner can be connected to the connecting portion 156 at another location. Additionally, it is preferable that the shapes of the slits 164 correspond to the shapes of the arms 160. For example, as shown in FIG. 3, both the arms 160 and the slits 164 are substantially straight. It will be appreciated by one skilled in the art, however, that without departing from the scope of the present invention, a slit can have a different shape than an arm. It will also be appreciated that the shapes of arms and slits can be different among the respective pluralities. In other words, some slits can be straight while others are not, and some arms can be straight while others are not. It will also be appreciated that, without departing from the scope of the present invention, a liner may not include a slit.

Figure 4:
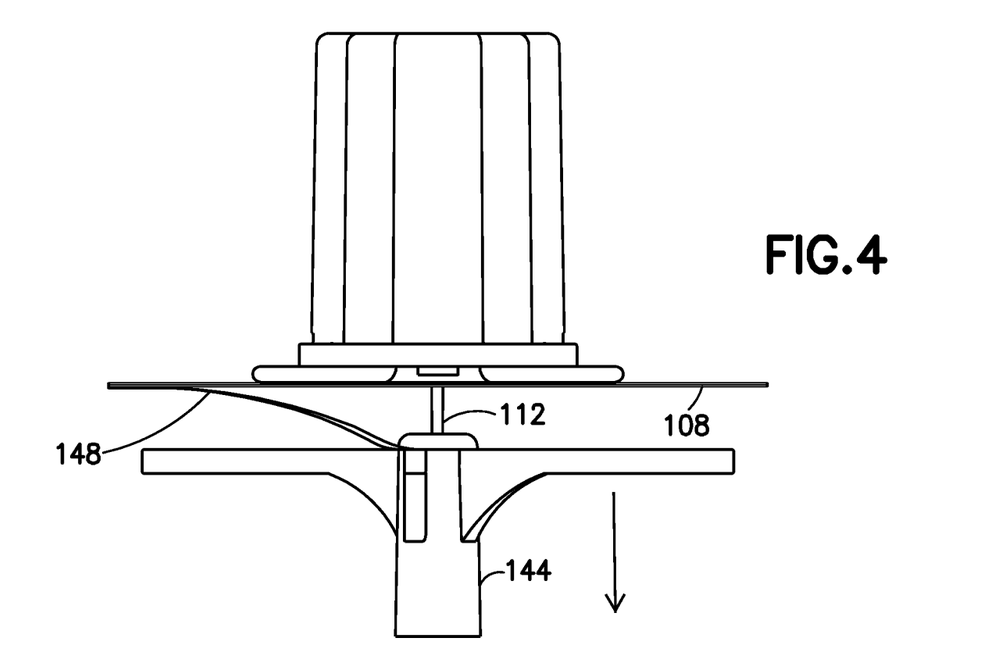
FIGS. 4-6 illustrate removal of the protector of FIG. 3.
Figure 5:
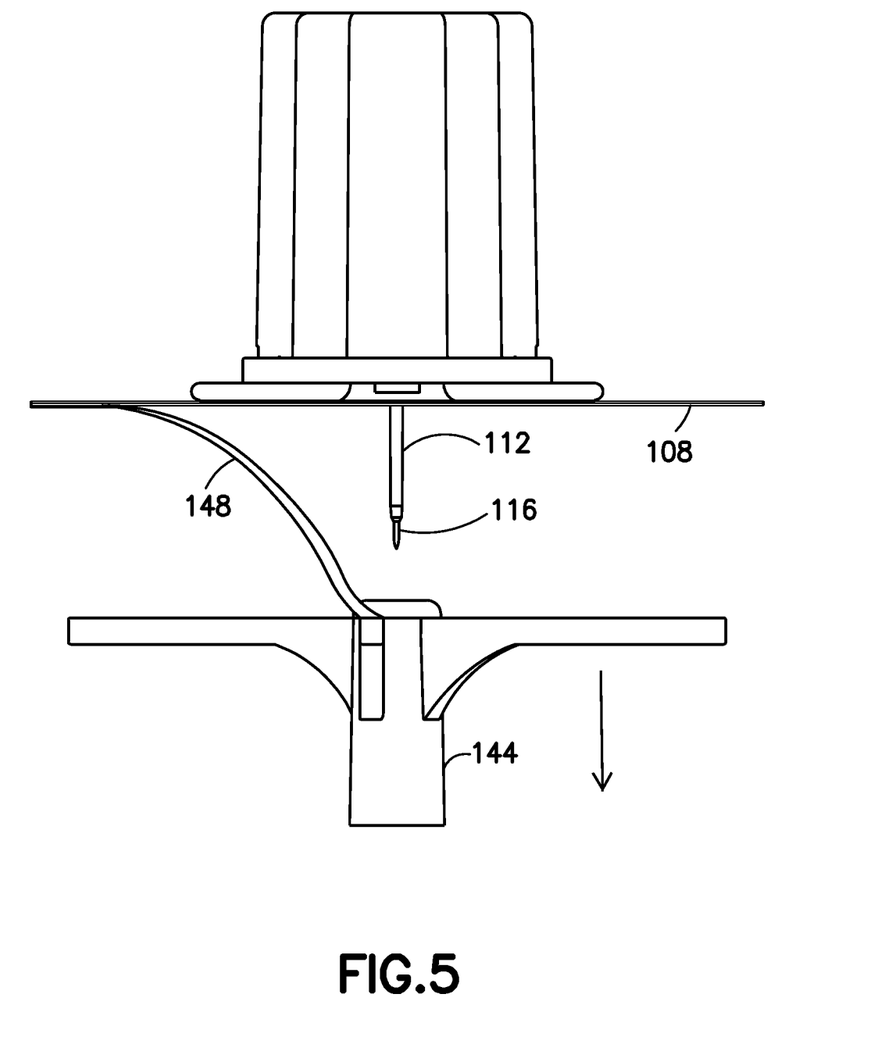
Figure 6:
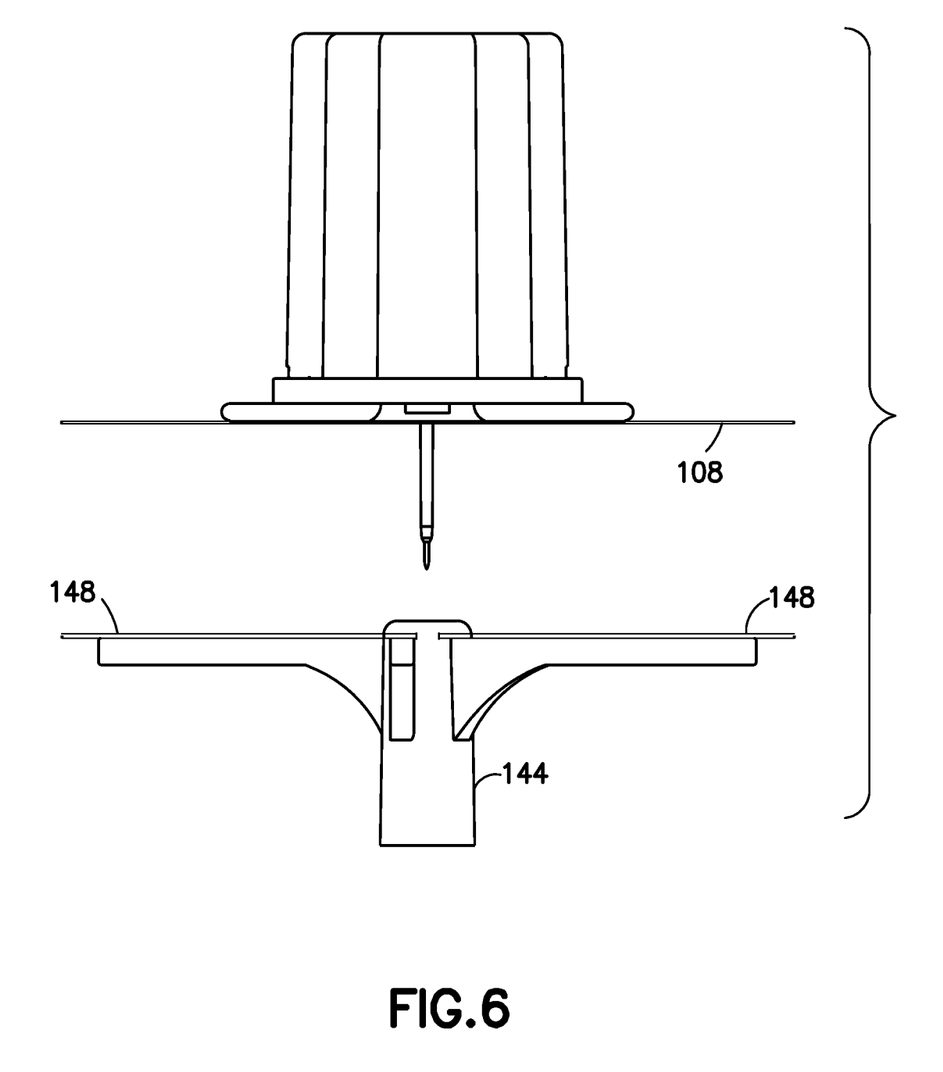
Figure 7:
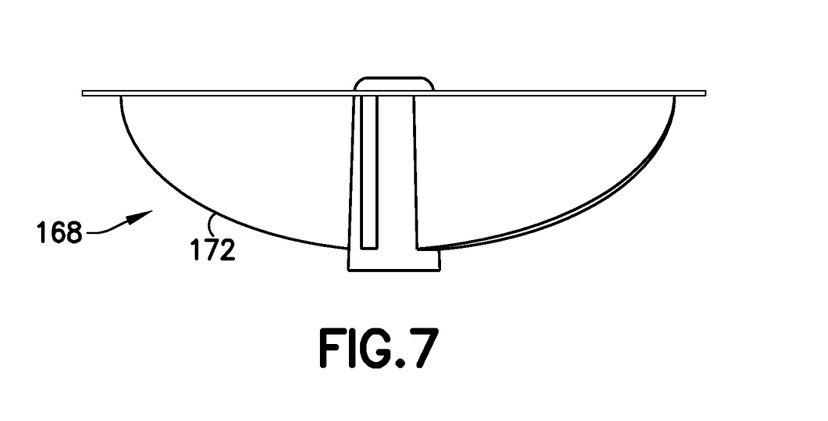
FIGS. 7-15 illustrate additional protectors in accordance with additional embodiments of the present invention.

In operation, to remove the protector 140, the user grasps the protector 140 and pulls axially (i.e., distally), or both rotates and pulls axially, thereby conjointly removing the connected guard 140 and adhesive liner 148. Because the guard 140 and the adhesive liner 148 are joined, removal of either the liner 148 or the guard 140 is conjoint with at least partial removal of the other. Put another way, according to one embodiment, removal of the liner 148 at least partially removes the guard 140, and vice versa. In the embodiment shown in FIGS. 4-6, the user pulls the protector 140 in a distal or downward direction. For clarity, in FIGS. 4 and 5, only one of the adhesive liners 148 is illustrated. In FIG. 4, the guard 144 still partially covers the cannula 112 and the needle 116, and the adhesive liner 148 is partially removed from the adhesive pad 108. In FIG. 5, the guard 144 no longer covers the cannula 112 and the needle 116, and the adhesive liner 148 is not yet completely removed from the adhesive pad 108. In FIG. 6, with continued distal movement of the guard 144, the adhesive liner 148 is completely removed from the adhesive pad 108.

It may be desirable to remove the liner 148 prior to completely removing the guard 140 to reduce the likelihood of a needle-stick injury. This can be accomplished by rotating the guard and pulling the guard 140 distally. The guard can then be completely removed by continuing to pull the guard 140 distally.

As another example, it may be desirable to completely remove the guard 140 prior to completely removing the liner 148. This can be accomplished with, for example, an accordion-like liner with several folds, particularly if the cannula is short. With such a liner, the guard can be distally pulled completely off of the cannula while the liner remains on the adhesive. But continued pulling removes the liner because the liner and the guard are connected. Such an accordion liner is an example of a type of "lost motion" connection in which there is a time delay between the action on one of the guard and the liner and the action on the remaining one of the guard and the liner. Put another way, as an example other than the accordion liner, some movement of the guard does not immediately remove the liner. According to one embodiment, however, removal of the guard 140 and the liner 148 is substantially simultaneous.

According to another embodiment, removal of the guard turns up a corner of the liner, allowing the user to easily grasp the turned-up corner to manually remove the liner.

As another example of operation, after the user installs the medical device 100 in an insertion device (not shown) and loads (for example, the spring) the insertion device, the user then removes the connected guard 140 and liner 148. This permits the user to load the insertion device without risking a needle-stick injury or risking degrading the adhesive prior to insertion.

Figure 8:
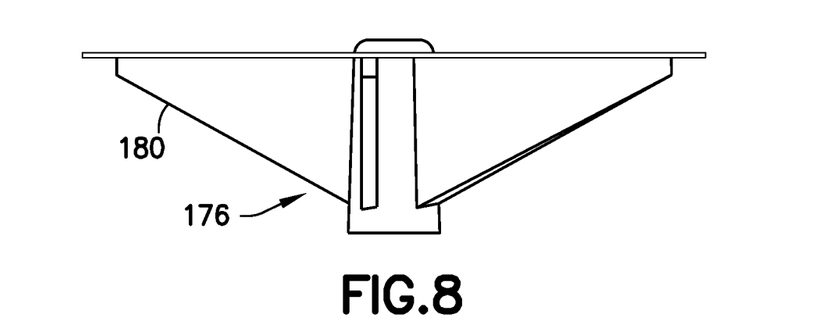
Figure 9:
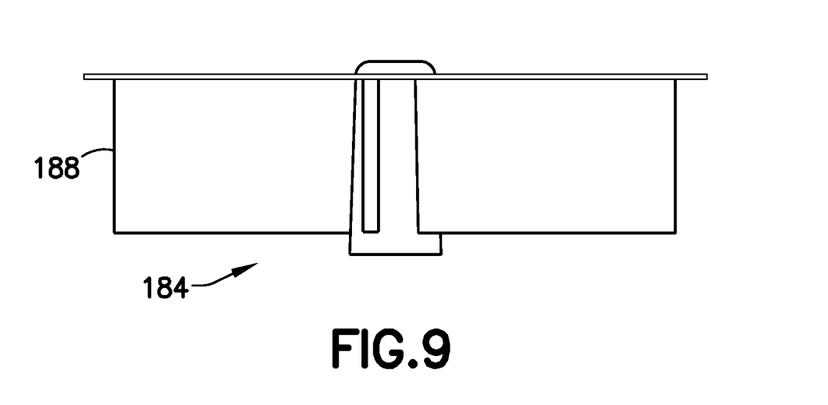
Figure 10:
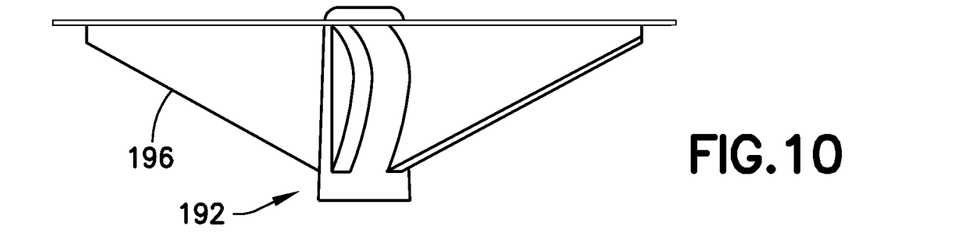

FIGS. 7-10 are perspective front views of protectors in accordance with alternative embodiments of the present invention. For example, in FIG. 7, the peripheral edges of the arms 172 of the protector 168 are curved. In FIG. 8, the arms 180 of the protector 176 are substantially triangular, and in FIG. 9, the arms 188 of the protector 184 are substantially rectangular. In contrast to the protectors 168, 176, and 184, in which the arms are substantially vertically straight, the arms 196 of the protector 192 in FIG. 10 curve along a vertical path. Such a design can provide a more contoured and comfortable fit with a user's fingers. Additionally, compared with the protector 140 of FIG. 3, each of the protectors 168, 176, 184, and 192 has an increased user gripping area to aid a user in grasping the protector.

Figure 11:
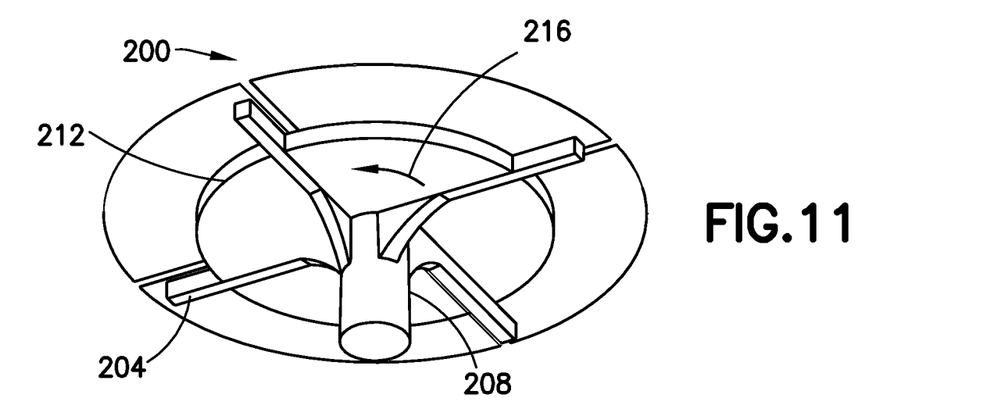

FIG. 11 is a perspective bottom view of a protector 200 in accordance with an embodiment of the present invention. Like the protector of FIG. 3, the protector 200 has a plurality of arms 204 extending from a guarding portion 208, but the arms 204 are joined by web portions 212. The web portions 212 can increase the stability of the arms 204. The web portions are illustrated as being sectors of a disc, but other web portions can be employed without departing from the scope of the present invention. For example, a web portion can be a bar or bars connecting adjacent arms 204. Such bars can be substantially straight, or can be curved. It will be appreciated that the adhesive liner 214 can be connected to the web portion, either instead of, or in addition to being connected to one or more of the arms 204.

The protector 200 also has an indicator 216 indicating a preferred direction for removal of the protector. For example, the indicator 216 can indicate a rotational direction. It will be understood that, without departing from the scope of the present invention, the indicator can indicate an axial direction, or there can be multiple indicators, for example, one indicator illustrating a rotational direction and one indicator illustrating an axial direction. Further, such multiple indicators can indicate a preferred order of operations.

Figure 12:
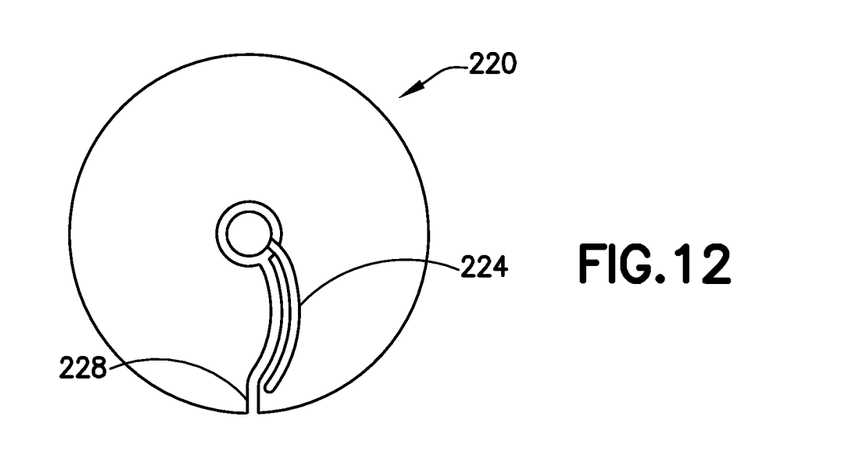
Figure 13:
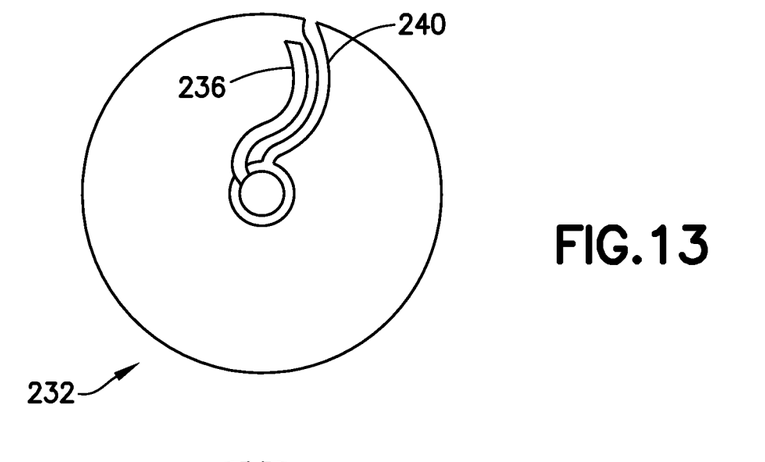

FIGS. 12-15 are bottom views of protectors in accordance with additional embodiments of the present invention. In FIG. 12, the protector 220 has a single, radially curved arm 224. The slit 228 is also curved. Similarly, in FIG. 13, the arm 236 and the slit 240 of the protector 232 is S-shaped. As with the protector of FIG. 10, the curved arm 224 and the S-shaped arm 236 can provide a more contoured and comfortable fit with a user's fingers.

Figure 14:
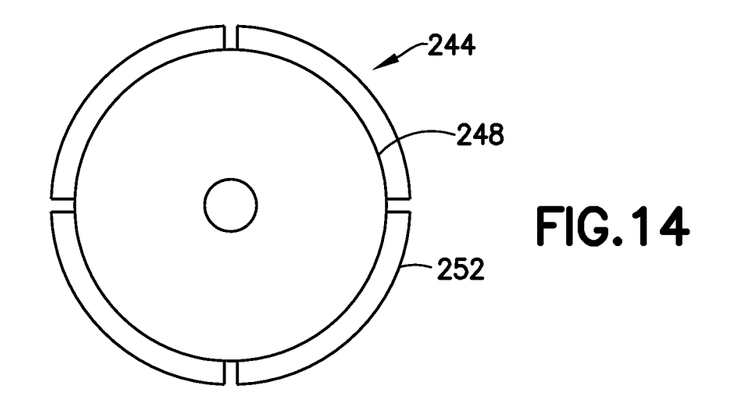
Figure 15:
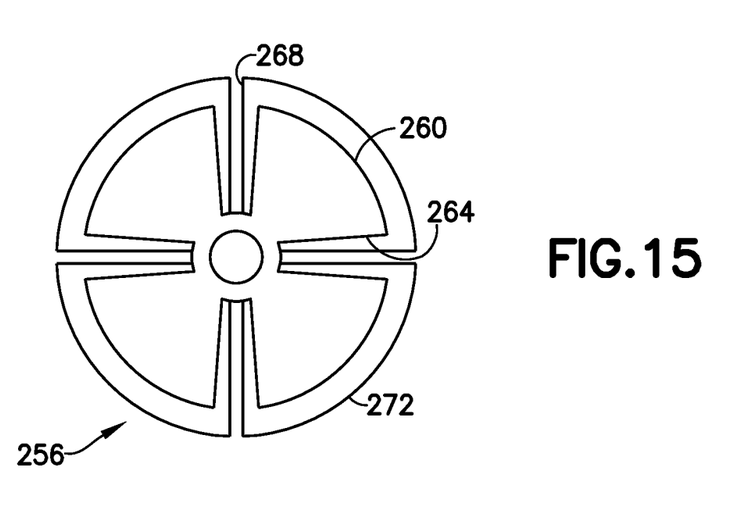

The connecting portion of the protector 244 in FIG. 14 includes a disc 248. Such an embodiment permits greater surface area connection between the connecting portion and the liner 252 than, for example, the arms 160 of FIG. 3. Similarly, in FIG. 15, the disc 260 of the protector 256 has cutout portions 264 that can reduce the amount of material of the guard. Such cutout portions 264 can be aligned with slits 268 of the liner 272 (as depicted in FIG. 15), or can be offset from the slits 268. According to one embodiment, however, the liner does not include a slit.

Although using adhesive or double-sided tape has been previously described for connecting the adhesive liner with the guard, other methods of connection can also be employed without departing from the scope of the present invention. For example, a mechanical fastener, such as a screw or pin can be used to secure the adhesive liner to the guard. Additionally, the guard can have a slit through which a portion of the liner is threaded or clamped. Further, a portion of the liner can be folded over a portion of the guard, for example, an arm. It will also be understood that the connection between the guard and the liner can be temporary. That is, subsequent to the removal of at least a portion of the protector, the guard and the liner can become disconnected. For example, if the liner is simply folded over an arm or arms of the guard, and the user rotates and/or distally pulls the guard until the liner is removed but the guard still protects a portion of the introducer needle and/or the cannula, the liner can fall away from the guard prior to the complete removal of the guard.

Moreover, although embodiments of the present invention have been described in conjunction with an infusion set, it will be appreciated that embodiments of the present invention can also be employed with patch pumps, IV catheters, continuous glucose monitoring devices, or other medical devices with an insertable cannula and an adhesive to secure the device to the patient's skin.

Embodiments of the present invention combine the steps of removing a cannula guard and peeling off an adhesive release liner into one single step. Because the liner and the guard are connected, either directly or indirectly, a user either pulls or twists and pulls the guard off the base and the liner is thereby also removed, or vice-versa. Particularly for an infusion set, the single-step removal can permit the adhesive liner to remain in place when the user places the infusion set into an insertion device and loads the insertions device (e.g., the spring), thereby avoiding catching the adhesive on the insertion device during these operations.

Although only a few embodiments of the present invention have been shown and described, the present invention is not limited to the described embodiments. Instead, it will be appreciated by those skilled in the art that changes may be made to these embodiments without departing from the principles and spirit of the invention, the scope of which is defined by the appended claims and their equivalents.

What is claimed is:

1. A medical device, comprising:
   a body;
   a cannula extending from the body, for insertion into a patient's skin;

a guard covering the cannula, the guard being open at opposing ends thereof and comprising a guarding portion adapted to cover the cannula, and a connecting portion;

an adhesive for securing the medical device to the patient's skin; and an adhesive liner covering the adhesive;

wherein:

the guard is connected to the adhesive liner to enable conjoint and at least partial removal of the guard and the adhesive liner;

the connecting portion is adapted to connect the guard to the adhesive liner and a top surface of the connecting portion is planar where the connecting portion contacts the adhesive liner;

the connecting portion comprises at least one curved, cantilevered arm extending from the guarding portion;

wherein the adhesive liner has a slit; and a shape of the slit matches a shape of the at least one arm.

2. The medical device according to claim 1, wherein the connecting portion comprises a plurality of arms.

3. The medical device according to claim 1, wherein the at least one arm has an S-shape.

4. The medical device according to claim 1, wherein:
the guard is connected to the adhesive liner at or adjacent to the slit.

5. The medical device according to claim 1, wherein at least one of the adhesive liner and the guard has an indicator indicating a direction for removal.

6. The medical device according to claim 1, wherein the guard and the adhesive liner are directly joined to each other.

7. The medical device according to claim 1, wherein the adhesive liner constitutes at least one segment of a multi-segment liner covering the adhesive.

8. The medical device according to claim 1, wherein during the conjoint and at least partial removal of the guard and the adhesive liner, there is a time delay between the at least partial removal of one of the guard and the adhesive liner and the at least partial removal of the remaining one of the guard and the adhesive liner.

9. A protector for a medical device, comprising:

a guard for guarding a cannula extending from a body of the medical device, the guard being open at opposing ends thereof and comprising a guarding portion adapted to cover the cannula, and a connecting portion; and an adhesive liner for covering an adhesive for securing the medical device to the patient's skin, the adhesive liner having a slit;

wherein the guard is connected to the adhesive liner to enable conjoint and at least partial removal of the guard and the adhesive liner;

wherein the connecting portion is adapted to connect the guard to the adhesive liner and a top surface of the connecting portion is planar where the connecting portion contacts the adhesive liner;

wherein the connecting portion comprises at least one curved, cantilevered arm extending from the guarding portion; and wherein a shape of the slit matches a shape of the at least one arm.

10. The protector according to claim 9, wherein the guard is connected to the adhesive liner adjacent to the slit.

11. The protector according to claim 9, wherein the guard and the adhesive liner are directly joined to each other.

12. The medical device according to claim 1, wherein the at least one cantilevered arm curves where it contacts the guarding portion to provide a gripping area contoured for a user's fingers.

13. The protector according to claim 9, wherein the at least one cantilevered arm curves where it contacts the guarding portion to provide a gripping area contoured for a user's fingers.

* * * * *